United States Patent [19]
Ozeki

[11] Patent Number: 5,846,964
[45] Date of Patent: Dec. 8, 1998

[54] HEPATITIS C VIRUS PROLIFERATION INHIBITOR

[75] Inventor: Tsuneo Ozeki, Kitakyushu, Japan

[73] Assignee: Tokyo Tanabe Company Limited, Tokyo, Japan

[21] Appl. No.: 586,633

[22] PCT Filed: Jul. 19, 1994

[86] PCT No.: PCT/JP94/01187

§ 371 Date: Jan. 18, 1996

§ 102(e) Date: Jan. 18, 1996

[87] PCT Pub. No.: WO95/03056

PCT Pub. Date: Feb. 2, 1995

[30] Foreign Application Priority Data

| Jul. 19, 1993 | [JP] | Japan | 5-178072 |
| Nov. 17, 1993 | [JP] | Japan | 5-288391 |

[51] Int. Cl.⁶ .................................................. A61K 31/56
[52] U.S. Cl. ............................................................ 514/182
[58] Field of Search ............................................ 514/182

[56] References Cited

U.S. PATENT DOCUMENTS

| 4,957,910 | 9/1990 | Sutton et al. | 514/182 |
| 5,234,697 | 8/1993 | Sipos | 424/490 |

FOREIGN PATENT DOCUMENTS

| 0 365 139 | 4/1990 | European Pat. Off. . |
| 0 513 887 | 11/1992 | European Pat. Off. . |
| 0 537 626 | 4/1993 | European Pat. Off. . |
| A-59-167517 | 9/1984 | Japan . |
| 62-77333 | 4/1987 | Japan . |
| A 63-301823 | 12/1988 | Japan . |
| A 2-142731 | 5/1990 | Japan . |
| A-2-167235 | 6/1990 | Japan . |
| A-4-500514 | 1/1992 | Japan . |
| A 4-500670 | 2/1992 | Japan . |
| A 5-508168 | 10/1992 | Japan . |
| A 4-349885 | 12/1992 | Japan . |
| A 5-142231 | 6/1993 | Japan . |

OTHER PUBLICATIONS

Martindale, The Extra Pharmacopoeia, 28th edition, pp. 646–647, 1982.
Biosis Abs. No. 93025780, Buzzelli et al., Curr. Ther. Res. 50(5), pp. 635–642, 1991.
Biosis Abs. No. 97220601, Bincze et al., Acta Physiologica Hungarcia, 80(1–4), pp. 369–374, 1992.
WPI Abs. No. 92–382037/46, of WO 92/18524, 1992.
G. Buzzelli, et al., "L'emisuccinato dell'acido ursodesossicolico nel trattamento dell'epatite cronica Attiva", Minerva Med, 1992, vol. 83, No. 9, pp. 537–540.
M. A. Garassini, et al., "Hepatitis Viral C", Gen, Oct. 1993, vol. 47, No. 4., pp. 257–273.
G. Buzzelli, et al., "Long–Term Treatment With Ursodeoxycholic Acid In Patients With Chronic Active Hepatitis", Current Therapeutic Research, Nov. 1991, vol. 50, No. 5, pp. 635–642.
Claudio Puoti, et al., "Ursodeoxycholic Acid And Chronic Hepatitis C Infection", The Lancet, May 29, 1993, vol. 341, No. 8857, pp. 1413–1414.
Mario Angelico, et al., "Recombinant Interferon–α and Ursodeoxycholic Acid versus Interferon–α Alone in the Treatment of Chronic Hepatitis C: A Randomized Clinical Trial with Long–term Follow–up", The American Journal of Gastroenterology, vol. 20, No. 2 (1995) pp. 263–269.
Eveline Boucher, et al., "Interferon and Ursodeoxycholic Acid Combined Therapy in the Treatment of Chronic Viral C Hepatitis: Results From a Controlled Randomized Trial in 80 Patients", Hepatology, vol. 21, No. 2, pp. 322–327 (1995).
The Lancet, 335, 1419–22 (1990) "Detection of Hepatitis C viral sequences in blood donations by nested polymerase chain reaction and prediction of infectivity" by J.A. Garson et al.
Antiviral Research, vol. 24, No. 2–3, (1994) pp. 245–257 "Prospectives on the treatment of chronic hepatitis B and chronic hepatitis C with thymic peptides and antiviral agents" Mutchnick, Milton G. et al.

Primary Examiner—Raymond Henley, III
Attorney, Agent, or Firm—Griffin, Butler, Whisenhunt & Szipl, LLP

[57] ABSTRACT

A hepatitis C virus proliferation inhibitor comprising a bile acid or a physiologically acceptable salt thereof is disclosed, as well as a method for treating a mammal infected with hepatitis C and a pharmaceutical composition for treating hepatitis C. As the bile acid to be used in the present invention, free bile acids, such as ursodeoxycholic acid and chenodeoxycholic acid, and conjugated bile acids such as tauroursodeoxycholic acid are exemplified. Also, as the physiologically acceptable salt, alkali metal salts such as the sodium salt of the bile acid is exemplified.

7 Claims, No Drawings

HEPATITIS C VIRUS PROLIFERATION INHIBITOR

This application is a 371 of PCT/JP94/01187 filed Jul. 19, 1994, published as WO95/03056 Feb. 2, 1995.

FIELD OF THE INVENTION

The present invention relates to a hepatitis C virus proliferation inhibitor containing bile acid as the active principle.

BACKGROUND ART

Hepatitis, which is neither hepatitis A nor hepatitis B, forms 95 to 100% of post-transfusion hepatitis and 40 to 50% of sporadic hepatitis and easily becomes chronic, further changing at high rates to cancer of liver via chronic hepatitis or hepatic cirrhosis. Recently, hepatitis C virus (hereinafter referred to as HCV) was identified, and it has been demonstrated that most of hepatitis previously known as non-hepatitis A or non-hepatitis B are caused by this hepatitis C virus.

Although interferon has been known as an agent having inhibitory effect on the proliferation of hepatitis C virus, it is pointed out that there are problems such as its low rate in the effectiveness as little as 30 to 40%, the 60 to 70% recrudescence after discontinuance of the dosage thereof, the appearance of influenza-like symptoms, such as pyrexia, headache and vomiting, and of diverse side effects such as leukopenia, at the high rates.

Bile acid is a drug being publicly known as a choleretic, liver function improving agent, etc. As examples of the inhibitory effect of bile acid on the proliferation of virus, the anti-viral activities against herpes virus, human immunodeficiency virus, influenza virus, parainfluenza virus, etc., have been known (see Japanese Patent Laid-opened Nos. Sho 59-167517 Gazette, Sho 63-301823 Gazette, Hei 2-167235 Gazette, Hei 4-500514 Gazette and Hei 4-500670 Gazette). However, it has not been known that bile acid has an inhibitory effect on the proliferation of hepatitis C virus. Although a suppository preparation comprising an ursodeoxycholic acid salt and interferon is disclosed in Japanese Patent Laid-opened No. Sho 62-77333 Gazette, the bile acid is used just as an absorption promoting agent in the dosage of interferon into colon or rectum, and therefore, the disclosure does not suggest at all that bile acid has an inhibitory effect on the proliferation of hepatitis C virus.

It is an object of the present invention to provide a novel and highly effective hepatitis C virus proliferation inhibitor which gives no adverse reaction.

DISCLOSURE OF THE INVENTION

As a consequence of enthusiastic investigation made by the inventors of the present invention on hepatitis C and hepatitis C virus, such inventors found that bile acid can show an inhibitory effect on the proliferation of hepatitis C virus and have subsequently accomplished the present invention. Namely, the present invention is directed to a hepatitis C virus proliferation inhibitor comprising bile acid or the physiologically acceptable salts thereof as the active principle.

As bile acid to be used in the present invention, free bile acid, such as ursodeoxycholic acid and chenodeoxycholic acid, or conjugated bile acid such as tauroursodeoxycholic acid can be exemplified. As the physiologically acceptable salt of bile acid, an alkali metal salt thereof such as the sodium salt can be exemplified. These salts can be prepared according to any of the methods for manufacturing bile acid widely known in the art.

As the administration route for the hepatitis C virus proliferation inhibitor according to the present invention, oral administration with any of tablets, capsules, granules, powders, medicated syrup, etc. or parenteral administration with injections,. suppositories, etc. can be exemplified. These pharmaceutical preparations can be prepared by combining with additives, such as fillers, binders, disintegrators, lubricants, stabilizers and correctives, and according to any of the methods widely known in the art. The dose range of the inhibitory agent for an adult per day, though subject to symptoms and ages of the patients as well as other factors, is normally from 800 to 3,000 mg, preferably from 1,200 to 1,800 mg, and more preferably from 1,400 to 1,600 mg, for oral administration, and from 30 to 1,200 mg, preferably from 50 to 1,000 mg, and more preferably from 100 to 600 mg, for parenteral administration, and the dosage can be made either at one time, or divided into several times a day. In the case of parenteral administration, it is preferable to dose the agent according to the intravenous drip infusion method.

BEST MODE FOR CARRYING OUT THE INVENTION

The results each obtained in inhibition tests on the proliferation of hepatitis C virus, clinical tests and acute toxicological tests with bile acid are described hereinafter in detail. For the bile acid, ursodeoxycholic acid (UDCA) and tauroursodeoxycholic acid (TUDCA) were used as the representative compound.

(Inhibition Test on Proliferation of Hepatitis C Virus)

Liver biopsy was carried out on six patients aged from 40 to 60 who are suffering chronic hepatitis C and positive to both HCV antibody and HCV RNA, and they are referred to as $S_1$, $S_2$, $S_3$, $S_4$, $S_5$ and $S_6$, respectively. Half of each liver specimen obtained from each of the patients, respectively, were then fixed with formalin and subsequently stained with HE and Azan to perform tissue diagnosis, while the remaining halves were subjected to grinding in a mortar with sea sand to obtain a supernatant. The supernatant was added into Eagle-MEM culture medium (added with 10% FCS) wherein Chang cells are cultured, then placed in 95% air containing 5% $CO_2$ maintained at 37° C. to complete the infection. The medium was then centrifuged at 1,800 rpm, and the cells precipitated were added into an Eagle-MEM culture medium (previously added with FCS and antibiotic) containing UDCA (the concentration in the medium: 25 and 50 $\mu$M), one containing TUDCA (the concentration in the medium: 20 and 50 $\mu$M) and one without UDCA or TUDC respectively, and then adjusted to the concentration of $1 \times 10^5$ cells/slide. The cells were cultivated on LAB-TEK Chamber slides for one week in the UDCA-containing medium and 2 weeks in the TUDCA-containing medium under 95% air containing 5% $CO_2$ maintained at 37° C.

The presence of HCV in these cultured Chang cells was firmly confirmed by the appearance of a band with 178 bp (base pair) by employing HCV RNA reverse transcription PCR method as described in Lancet Vol. 335, pages 1419–22, 1990. Also, the infection rate of HCV to the Chang cells was determined by immunologically staining HCV by using core antibody (Okayama's monoclonal antibody) and by counting the positive cells under an optical microscope.

For the immunological staining, the ABC method using HRS was employed, wherein HRS is the abbreviation of Horse Radish staining, while ABC is the abbreviation of Avidin-Biotin Complex. In addition, the infection of HCV to the Chang cells was also confirmed according to in situ hybridization method, separately.

The results of the inhibition test on the proliferation of HCV with UDCA and TUDCA are shown in Tables 1 and 2, respectively. The control in the tables shows the result obtained by subjecting to the same procedure except without the addition of the supernatant.

TABLE 1

Result of Inhibition Test on Proliferation of HCV with UDCA (Infection Rate: %)

| | Concentration of UDCA | | |
|---|---|---|---|
| | 0 $\mu$M | 25 $\mu$M | 50 $\mu$M |
| Control | 29.7 ± 5.5 | 21.4 ± 0.9 | 22.2 ± 4.1 |
| Patient $S_1$ | 45.2 ± 4.2 | 35.6 ± 8.1 | 16.6 ± 2.0 |
| Patient $S_2$ | 50.1 ± 7.4 | 23.9 ± 7.0 | 17.2 ± 3.3 |
| Patient $S_3$ | 38.9 ± 8.2 | 27.0 ± 6.2 | 18.5 ± 2.8 |

TABLE 2

Result of Inhibition Test on Proliferation of HCV with TUDCA (Infection Rate: %)

| | Concentration of TUDCA | | |
|---|---|---|---|
| | 0 $\mu$M | 20 $\mu$M | 30 $\mu$M |
| Control | 8.4 ± 3.6 | 5.5 ± 5.0 | 2.8 ± 0.6 |
| Patient $S_4$ | 38.8 ± 7.1 | 32.8 ± 22.4 | 13.5 ± 8.1 |
| Patient $S_5$ | 18.2 ± 3.3 | 6.9 ± 3.4 | 6.8 ± 0.7 |
| Patient $S_6$ | 25.6 ± 7.3 | 9.3 ± 3.8 | 5.5 ± 1.2 |

As can be clearly seen in the Tables 1 and 2 shown above, the proliferation of HCV was significantly inhibited in both groups containing UDCA and TUDCA, respectively, in comparison with the group not containing UDCA or TUDCA.

(Clinical Test)

Each of 8 patients aged from 52 to 72 suffering from chronic hepatitis C, who are referred to $S_7$, $S_8$, $S_9$, $S_{10}$, $S_{11}$, $S_{12}$, $S_{13}$ and $S_{14}$, respectively, was orally administered with UDCA at a dose of from 1,200 to 1,500 mg/day for a period of from 0.5 to 6 months. The quantitative values of HCV RNA in the serum of each of the patients before and after the dosage with UDGA were shown in Table 3.

TABLE 3

Quantitative Value of HCV RNA in Serum before and after Dosage with UDCA

| | Dose (mg/day) | Dosage Period (Month) | Quantitative Value of HCV RNA in Serum | |
|---|---|---|---|---|
| | | | Before Dosage | After Dosage |
| Patient $S_7$ (Female, Age 58) | 1500 | 1 | $10^9$/ml | $10^7$/ml |
| Patient $S_8$ (Male, Age 65) | 1500 | 1 | $10^3$/ml | 0/ml |
| Patient $S_9$ (Male, Age 59) | 1200–1500 | 6 | $10^{10}$/ml | $10^{6.5}$/ml |

TABLE 3-continued

Quantitative Value of HCV RNA in Serum before and after Dosage with UDCA

| | Dose (mg/day) | Dosage Period (Month) | Quantitative Value of HCV RNA in Serum | |
|---|---|---|---|---|
| | | | Before Dosage | After Dosage |
| Patient $S_{10}$ (Female, Age 72) | 1200–1500 | 5 | $10^{10}$/ml | $10^6$/ml |
| Patient $S_{11}$ (Female, Age 60) | 1500 | 1.5 | $10^{10}$/ml | $10^6$/ml |
| Patient $S_{12}$ (Female, Age 67) | 1500 | 2 | $10^{10}$/ml | $10^{6.5}$/ml |
| Patient $S_{13}$ (Male, Age 57) | 1500 | 0.5 | $10^4$/ml | 0/ml |
| Patient $S_{14}$ (Male, Age 52) | 1200–1500 | 3 | $10^4$/ml | 0/ml |

As can be clearly seen from the Table 3 shown above, the proliferation of HCV in the patients suffering chronic hepatitis C was remarkably inhibited by dosage with UDCA.

(Acute Toxicological Test)

Acute toxicological tests were carried out by using male and female Wistar-strain rats aged 9 weeks and male and female dd-strain mice aged 8 weeks for UDCA, and by using male and female Beagle dogs aged from 8 to 11 months and male and female SD-strain rats aged 6 weeks for TUDCA to obtain $LD_{50}$, respectively. The results are shown in Tables 4 and 5, respectively.

TABLE 4

Result of Acute Toxicological Test on UDCA [$LD_{50}$ (mg/Kg)]

| | | Rats | | Mice | |
|---|---|---|---|---|---|
| | | Male | Female | Male | Female |
| UDCA | Oral | >5000 | >5000 | >10000 | >10000 |
| | Intravenous | 310 | 320 | 285 | 240 |

TABLE 5

Result of Acute Toxicological Test on TUDCA [$LD_{50}$ (mg/Kg)]

| | | Beagle Dogs | | Rats | |
|---|---|---|---|---|---|
| | | Male | Female | Male | Female |
| TUDCA | Oral | >5000 | >5000 | >10000 | >10000 |
| | Intravenous | 300–600 | 300–600 | 600–800 | 600–800 |

As can be clearly seen from the Tables 4 and 5 shown above, both acute toxicity of UDCA and TUDCA are very low, proving that these can be a safe drug.

UTILIZATION IN THE INDUSTRY

It was demonstrated that bile acid can remarkably inhibit the proliferation of hepatitis C virus and is less toxic, and therefore, bile acid can be useful as a hepatitis C virus proliferation inhibitor.

What is claimed is:

1. A method of inhibiting hepatitis C proliferation in a mammal infected with hepatitis C virus, comprising administering to the mammal a dosage consisting essentially of tauroursodeoxycholic acid or a physiologically acceptable salt thereof effective to inhibit hepatitis C proliferation.

2. A method according to claim 1, wherein said step of administering comprises oral administration in a dose range of 800 to 3,000 mg/day.

3. A method of inhibiting hepatitis C proliferation in a mammal infected with hepatitis C virus, comprising administering to the mammal a dosage consisting essentially of chenodeoxycholic acid or a physiologically acceptable salt thereof effective to inhibit hepatitis C proliferation.

4. A method according to claim 3, wherein said step of administering comprises oral administration in a dose range of 800 to 3,000 mg/day.

5. A method of inhibiting hepatitis C proliferation in a mammal infected with hepatitis C virus, comprising administering to the mammal a dosage of bile acid or a physiologically acceptable salt thereof effective to inhibit hepatitis C proliferation, wherein said step of administering comprises oral administration in a dose range of 800 to 3,000 mg/day.

6. A method according to claim 5, wherein said dose range comprises 1,200 to 1,800 mg/day.

7. A method according to claim 5, wherein said dose range comprises 1,400 to 1,600 mg/day.

* * * * *